(12) United States Patent
Jbach et al.

(10) Patent No.: US 10,179,757 B2
(45) Date of Patent: Jan. 15, 2019

(54) PROCESS FOR OBTAINING A FORMATE FROM A REACTION MIXTURE

(71) Applicant: JBACH GMBH, Bischberg (DE)

(72) Inventors: Hermann Wolf Jbach, Bischberg (DE); Carmen Platten, Knetzgau (DE); Gunthard Scholz, Gundelsheim (DE); Andreas Bösmann, Heßdorf (DE)

(73) Assignee: JBACH GMBH, Bischberg (DE)

( * ) Notice: Subject to any disclaimer, the term of this patent is extended or adjusted under 35 U.S.C. 154(b) by 0 days.

(21) Appl. No.: 15/527,656

(22) PCT Filed: Nov. 18, 2014

(86) PCT No.: PCT/EP2014/074930
§ 371 (c)(1),
(2) Date: May 17, 2017

(87) PCT Pub. No.: WO2016/078698
PCT Pub. Date: May 26, 2016

(65) Prior Publication Data
US 2017/0327451 A1    Nov. 16, 2017

(51) Int. Cl.
| | | |
|---|---|---|
| *C07C 53/02* | (2006.01) | |
| *C07C 51/23* | (2006.01) | |
| *C07C 51/41* | (2006.01) | |
| *C07C 51/44* | (2006.01) | |
| *C01F 5/14* | (2006.01) | |
| *C01G 39/00* | (2006.01) | |
| *C07C 51/215* | (2006.01) | |
| *C02F 1/04* | (2006.01) | |
| *C02F 1/44* | (2006.01) | |

(52) U.S. Cl.
CPC .............. *C07C 53/02* (2013.01); *C01F 5/14* (2013.01); *C01G 39/006* (2013.01); *C07C 51/215* (2013.01); *C07C 51/23* (2013.01); *C07C 51/412* (2013.01); *C07C 51/44* (2013.01); *C02F 1/048* (2013.01); *C02F 1/441* (2013.01)

(58) Field of Classification Search
CPC ..... C07C 51/412; C07C 53/02; C07C 51/215; C07C 51/44; C07C 53/06; C07C 51/23; C07C 51/50; C01F 5/14; C01G 39/006; C02F 1/048; C02F 1/441
See application file for complete search history.

(56) References Cited

U.S. PATENT DOCUMENTS

| | | | | |
|---|---|---|---|---|
| 4,177,075 A | * | 12/1979 | Mansukhani | .......... C09D 11/36 106/31.06 |
| 2011/0098490 A1 | | 4/2011 | Reunanen et al. | |
| 2013/0245319 A1 | * | 9/2013 | Bosmann | ................ C07C 51/23 562/531 |

FOREIGN PATENT DOCUMENTS

| | | | |
|---|---|---|---|
| GB | 1072794 | * | 6/1967 |
| WO | 2009/130387 A2 | | 10/2009 |
| WO | WO2009130387 | * | 10/2009 |
| WO | 2012/034839 A1 | | 3/2012 |

OTHER PUBLICATIONS

International Search Report dated Jul. 2, 2015 in PCT/EP2014/074930 (5 pages).
Written Opinion dated Jul. 2, 2015 in PCT/EP2014/074930 (5 pages).
Response to Written Opinion filed Sep. 15, 2016 in PCT/EP2014/074930 (15 pages) (English translation of amended p. 1 of the specification and of the amended claims attached).
International Preliminary Report on Patentability (IPRP) dated Oct. 26, 2016 in PCT/EP2014/074930 (6 pages).

* cited by examiner

*Primary Examiner* — Yevgeny Valenrod
*Assistant Examiner* — Blaine G Doletski
(74) *Attorney, Agent, or Firm* — Prismatic Law Group PLLC

(57) ABSTRACT

The invention relates to a process for obtaining a formate from a reaction mixture (10) in which a polyoxometallate ion, which acts as a catalyst, is in contact with an organic material at a temperature below 120° C. to produce formic acid in an aqueous solution, with the following steps: a) separating a mixture of formic acid and water from the reaction mixture by reverse osmosis and/or as vapor (18), the vapor (18) subsequently being condensed, and b) reacting the formic acid with a hydroxide (24) in aqueous solution to produce a solution of a formate.

16 Claims, 2 Drawing Sheets

PROCESS FOR OBTAINING A FORMATE FROM A REACTION MIXTURE

Figure 1:
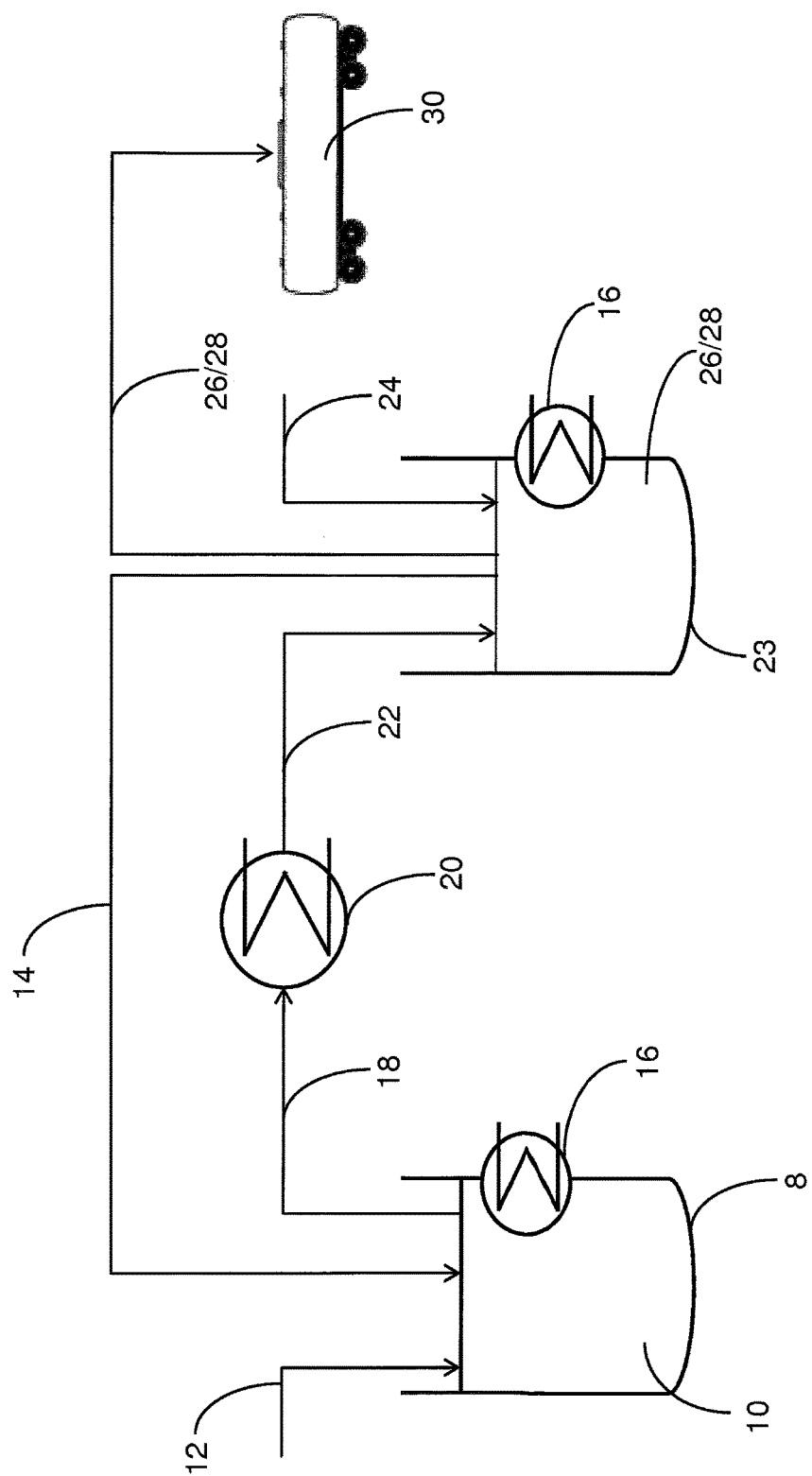

The present invention is filed under 35 U.S.C. § 371 as the U.S. national phase of International Patent Application No. PCT/EP2014/074930, filed Nov. 18, 2014, which designated the United States and which is hereby incorporated in its entirety including all tables, figures and claims.

The invention relates to a process for obtaining a formate from a reaction mixture in which a polyoxometallate ion, which acts as a catalyst, is in contact with an organic material at a temperature below 120° C. to produce formic acid in an aqueous solution.

Such a reaction mixture is known from WO 2012/034839 A1. WO 2012/034839 A1 relates to a process for catalytically producing formic acid, wherein a polyoxometallate ion, which is used as a catalyst, of the general formula $[PMo_xV_yO_{40}]^{5-}$ is brought into contact with an alpha-hydroxyaldehyde, an alpha-hydroxycarboxylic acid, a carbohydrate, or a glycoside in an aqueous solution at a temperature below 120° C., wherein $6<x<11$, $1<y<6$, $x+y=12$, and x and y are each a whole number. Such a solution can also be used as a reaction mixture in the process according to the invention. The formic acid produced in the process according to WO 2012/034839 A1 can be removed from the solution by distillation, reactive distillation, or extraction, in particular together with the catalyst, in particular by reacting with a base, in particular an amine, or by stripping. An ether or an amide can be added for extraction. A process by which the formic acid produced can be continuously removed from the reaction mixture during implementation of the process is not provided, however.

From US 2011/0098490 A1 a process is known for separating and recovering a formate from an aqueous liquid mixture comprising formic acid, levulinic acid, and optionally furfural. The mixture is subjected to a liquid-liquid extraction, resulting in an organic phase with the extracting agent, formic acid, levulinic acid, and optionally furfural and water and at least an aqueous phase comprising at least one inorganic acid. The aqueous phase is separated from the organic phase.

Formic acid is separated from the organic phase by distillation and is obtained in the form of a formate from the organic phase by subsequent neutralization.

A process is known from EP 0 038 317 B1 for producing essentially furfural, formic acid, acetic acid, and other organic compounds from acidic hydrolysates of plants. Here hydrolysate is introduced to a reaction and heated therein to a temperature above 200° C. Furfural, formic acid, and acetic acid are then obtained as distillate and then optionally extracted with an extracting agent. At such a temperature however the breakdown of formic acid already occurs, to carbon monoxide and water, for example.

None of the named documents discloses a process that allows continuous production of a formate from a reaction mixture in which formic acid is formed. "Continuous production of a formate" is understood to mean formate production that occurs at least during a predominant portion of the time in which formic acid also occurs in the reaction mixture. The object of the present invention is to provide a process that permits continuous production of a formate reaction in which formic acid is produced at the same time.

The object is achieved by the features of patent claim 1. Advantageous embodiments arise from the features of patent claims 2 to 11.

According to the invention, a process is provided for obtaining a formate from a reaction mixture. In the reaction mixture a polyoxometallate ion, which is used as a catalyst, of the general formula $[PMo_xV_yO_{40}]^{n-}$ is in contact with an organic material at a temperature below 120° C. to produce formic acid in an aqueous solution. Here $6 \leq x \leq 11$, $1 \leq y \leq 6$, $x+y=12$ and $3<n<10$, wherein n, x and y are each a whole number. In one embodiment of the process, $n=3+y$. Depending on the conditions in the reaction mixture, however, for example the pH value and the charge n can also assume other integer values from 4 to 9. In this sense a polyoxometallate ion is also understood to mean a plurality of identical polyoxometallate ions. The process comprises the following steps:

a) separating a mixture of formic acid and water out of the reaction mixture by reverse osmosis and/or as vapor, the vapor subsequently being condensed, b) reacting the formic acid with a hydroxide in aqueous solution to form a solution of a formate.

The vapor can be condensed using a cooler for distillation purposes, for example a Liebig condenser. The formic acid in step b) is the formic acid in the mixture of formic acid and water separated according to step a). The formic acid need not be separated from the mixture of formic acid and water to react with the hydroxide. The solution obtained in step b) can be concentrated by separating water by reverse osmosis and/or by partial or complete evaporation of the water. Evaporation in step c) can be carried out until the formate is dry. A surfactant or other additive, in particular sulfonic acid, in particular methanesulfonic acid, trifluoromethanesulfonic acid, camphorsulfonic acid, toluenesulfonic acid, in particular para-toluene sulfonic acid, chlorosulfonic acid, xylenesulfonic acid, benzenesulfonic acid or a derivative of one of the said acids, in particular chlorobenzenesulfonic acid, in particular para-chlorobenzene sulfonic acid, or a salt of the said acids or of the derivative, or any other substance which forms one of the said acids in an aqueous solution may be added to the reaction mixture. In this way the organic material, in particular waste paper, wood, or bacteria can be reacted better. Thus a better yield can be achieved.

The inventor of the present invention realized that formate, which is commercially traded in large quantities as a deicing agent, for example, can be produced much more simply directly than it is indirectly via isolation of formic acid. He further realized that in order to obtain formates in a first reaction step, it is not necessary to separate formic acid from the water that forms an azeotropic mixture with it. The inventor also realized that it is readily possible to separate a formic acid vapor-water vapor mixture from a reaction mixture at a temperature less than 120° C., wherein the reaction mixture comprises an organic material and a polyoxometallate ion used as a catalyst, both of which remain in the reaction mixture at separation. Here the reaction mixture can be an aqueous solution such as that used in WO 2012/034839 A1 for catalytic production of formic acid. The great advantage of the process is that the actual reaction in which the formic acid is produced in the reaction mixture does not have to be interrupted for separation of the vapor mixture, and can be sustained continuously. The further production of formic acid is also supported by continuous removal of formic acid from the reaction equilibrium.

In one embodiment of the process according to the invention, additional water and/or the water separated in step c) is added to the reaction mixture to compensate for the water separated in step a). In this way, a necessary or favorable concentration ratio for forming formic acid is maintained in the reaction mixture during the process.

In a further embodiment of the process according to the invention, further organic material is added to the reaction mixture to compensate for the reacted organic material. The further organic material can here be identical to the organic material originally contained in the reaction mixture. The continuous production of the formate can hereby be extended over a longer period of time.

Maintenance of contact of the organic material with the catalyst and/or the separation as vapor according to step a) can occur at a temperature of 15 to 119.5° C., in particular 40 to 95° C., in particular 50 to 85° C., in particular 55 to 85° C., in particular 60 to 83° C. At this temperature, the reaction temperature in the reaction mixture is sufficiently high to allow rapid formation of formic acid. A temperature in the range of 60 to 83° C. is advantageous as here the difference in the vapor pressure between formic acid and water is the greatest, wherein the formic acid has the higher vapor pressure. This causes the proportion of formic acid vapor in a formic acid vapor-water vapor mixture separated at this temperature to be relatively high. In order to allow effective evaporation at a temperature below 100° C., a reduction in the pressure acting on the reaction mixture is necessary. In one embodiment of the process according to the invention, the separation as vapor according to step a) therefore takes place at a pressure lower than atmospheric.

The organic material can be an alpha-hydroxyaldehyde, alpha-hydroxycarboxylic acid, carbohydrate, or glycoside, as is known from WO 2012/034839 A1. Alpha-hydroxyaldehydes, carbohydrates, and glycosides are present in a large number of renewable resources such as starch, cellulose, or hemicellulose. Starch, cellulose, and hemicellulose are obtained in large quantities as a product of crops or industrial pulping, for example for paper production.

The alpha-hydroxyaldehyde, alpha-hydroxycarboxylic acid, carbohydrate, or glycoside may be a monosaccharide, particularly an aldose, disaccharide, oligosaccharide or polysaccharide, starch, cellulose, hemicellulose, glucose, sucrose, xylose, cellobiose, xylan, hetereooligosaccharide, heteropolysaccharide, glycolic acid or lactic acid, or alpha-hydroxy aldehyde, alpha-hydroxycarboxylic acid, carbohydrate, or glycoside-containing residues or, in particular renewable, especially untreated raw materials. Untreated means that it has not previously been pulped. The residual material or renewable raw material can be a plant, fungus or bacteria, or components of plants, fungi or bacteria, wood, in particular in the form of wood flour or wood shavings, paper, especially waste paper, algae, cyanobacteria, or silage. The alpha-hydroxy aldehyde, alpha-hydroxycarboxylic acid, carbohydrate, or glycoside may also comprise a mixture of at least two of said substances or have been formed from at least one of said substances or the mixture. The alpha-hydroxyaldehyde, the alpha-hydroxycarboxylic acid, carbohydrate, or glycoside can also comprise a mixture of at least two of the named substances or can be made from at least one of the named substances or the mixture.

Many of the raw materials are obtained as byproducts, for example in paper production and wood processing. They are thus available as a more favorable starting material for the process according to the invention. The process according to the invention can thereby be performed very inexpensively.

The process according to the invention requires an especially low equipment expense when condensation of the vapor according to step a) is carried out by introducing the vapor into water, an aqueous solution, or the aqueous solution according to b), that is, an aqueous hydroxide solution. The desired formate is immediately produced in the case of an aqueous hydroxide solution. The hydroxide can be ammonium hydroxide, aluminum hydroxide, copper hydroxide, nickel hydroxide, an alkaline earth metal hydroxide, an alkali metal hydroxide, calcium hydroxide, magnesium hydroxide, sodium hydroxide, potassium hydroxide, or cesium hydroxide. Ammonium hydroxide has the particular advantage that ammonium hydroxide that is not reacted with formic acid can be separated from the resulting ammonium formate during or after step c) by evaporation. Separation of the unreacted hydroxide is not required if the hydroxide in step b) is used in a stoichiometric ratio to formic acid such that it is reacted completely or at least almost completely. Complete reaction of the hydroxide can also be achieved if it is used in a substoichiometric amount relative to the formic acid. Here the remaining, unreacted formic acid depending on the planned use is no hindrance or can be separated in step c) along with the water. With nearly complete reaction of the hydroxide, a remnant of the hydroxide does remain in the formate that is produced, but this is also no hindrance depending on the planned use.

Figure 2:
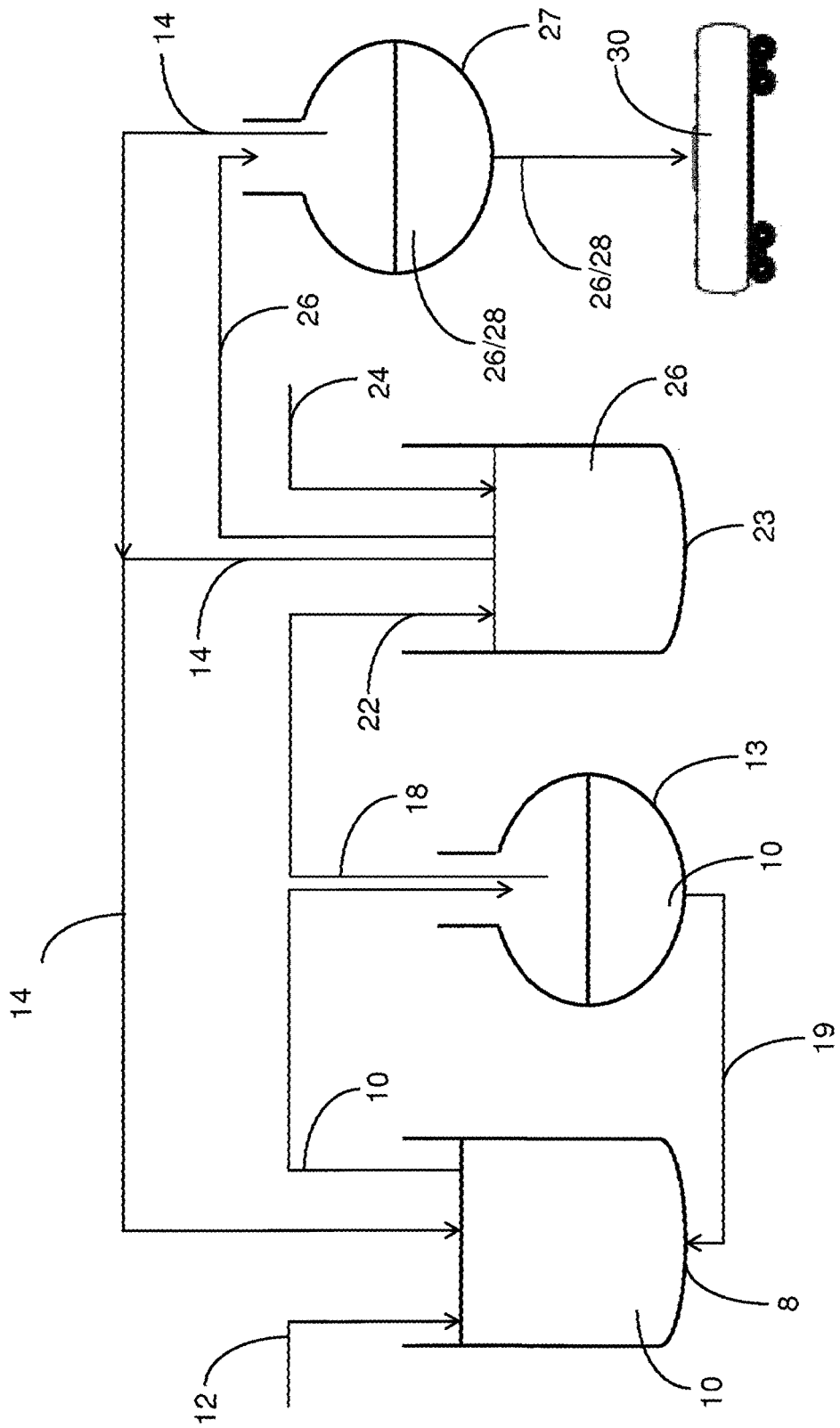

The invention is explained more closely below with reference to a drawing and an exemplary embodiment:

Wherein:

FIG. 1 is a schematic representation of a simply designed process according to the invention and FIG. 2 is a schematic representation of a further embodiment of the process according to the invention.

The schematic representation according to FIG. 1 shows a first vessel 8 containing a reaction mixture 10. The reaction mixture 10 comprises water, polyoxometallate ions as catalyst, an organic material, and formic acid produced from the organic material by means of the catalyst. The reaction mixture is maintained at a temperature range between 78° C. and 82° C. by means of a heat exchanger 16. Depending on the substrate, the catalyst used, amount of catalyst used, and degree of oxidation of the catalyst used it may be necessary to increase or decrease the heat supply to the reaction mixture. The pressure in the reaction mixture is reduced far enough below atmospheric pressure that a formic acid vapor-water vapor mixture 18 evaporates effectively in this temperature range. The formic acid vapor-water vapor mixture 18 is condensed by means of the cooler 20 to the formic acid-water mixture 22, which is stored in a second vessel 23. Further organic material 12 is added to compensate for the organic material reacted in producing the formic acid.

Hydroxide 24, for example in the form of a potassium hydroxide solution or a solid potassium hydroxide, is added to the formic acid-water mixture 22 in the second vessel. In the second vessel 23 this effects an exothermic neutralization of the formic acid, producing a formate. If and to the extent that it is still necessary because of the exothermic reaction, the resulting formate-water mixture 26 is heated by means of the heat exchanger 16, so that water vapor 14 is produced and after condensation in a cooler, not shown here, can be returned to the reaction mixture 10. Formate or a concentrated formate solution 28 remains in the second vessel and can be transferred to a transport trolley or tank truck 30 for removal.

In the further embodiment of the process according to the invention according to FIG. 2, a portion of the reaction mixture 10 is removed from the vessel 8, which contains the reaction mixture 10, maintained in a temperature range of around 92° C. to 97° C. by means of a heat exchanger, not shown, and is transferred to a first distillation vessel 13. There the reaction mixture 10 is maintained at lower than atmospheric pressure in a temperature range of around 78° C. to 82° C. by means of a heat exchanger, likewise not shown here, so that a formic acid vapor-water vapor mixture 18 is produced. The formic acid vapor-water vapor mixture 18 escapes the first distillation vessel 13 via a pipe and is condensed to a formic acid-water mixture 22 in a cooler, not shown here, and delivered to the second vessel 23. The remaining water, polyoxometallate ions, and organic material as well as a residue 19 containing a remnant of formic acid is returned to the reaction mixture 10 in the first vessel. Further organic material 12 is supplied to the reaction mixture 10 to compensate for the organic material reacted in the reaction.

A hydroxide 24 is added to the formic acid-water mixture 22 in the second vessel 23, so that a formate is produced during the resultant neutralization. Since this neutralization is exothermic, the formate-water mixture is heated in the process. The resulting water vapor 14 can be returned to the reaction mixture 10 after condensation by means of the cooler, not shown here. The formate-water mixture from the second vessel 10 is supplied to a second distillation vessel 27. If and to the extent that it is necessary, the formate-water mixture 26 is heated by means of a heater, not shown here, so that the water 14 contained in the formate-water mixture 26, possibly under reduced pressure, escapes as water vapor. After condensation in a cooler, not shown here, the water 14 is supplied to the reaction mixture 10. The formate-water mixture 26 can be vaporized in the second distillation vessel 27 until the formate is present in crystalline form. The remaining formate or concentrated formate solution 28 is transferred from the second distillation vessel 27 to a transport trolley or tank truck 30 for removal.

The process according to FIG. 2 is higher in equipment expense than the process according to FIG. 1, but has the advantage that the temperature for evaporation of the formic acid vapor-water vapor mixture 18 can be chosen independently of the reaction temperature in the first vessel 8. Thus a higher temperature and therefore higher reaction speed in the first vessel 8 can be selected than is favorable for evaporation of a formic acid vapor-water vapor mixture 18 with the largest possible proportion of formic acid.

REFERENCE SIGNS 8 first vessel
10 reaction mixture
12 further organic material
13 first distillation vessel
14 water/water vapor
16 heat exchanger
18 formic acid vapor-water vapor mixture
19 residue
20 cooler
22 formic acid-water mixture
23 second vessel
24 hydroxide
26 formate-water mixture
27 second distillation vessel
28 concentrated formate solution
30 tank truck

What is claimed is:

1. A method for obtaining a formate from a reaction mixture, in which a polyoxometallate ion, which acts as a catalyst, of the general formula $[PMo_x V_y O_{40}]^{n-}$ is in contact with an organic material at a temperature below 120° C. to produce formic acid in an aqueous solution, wherein $6 \leq x \leq 11$, $1 \leq y \leq 6$, $x+y=12$ and $3<n<10$, wherein n, x and y are each a whole number, which method comprises the following steps:

a) separating a mixture of formic acid and water from the reaction mixture by reverse osmosis and/or as vapor, the vapor subsequently being condensed and b) reacting the formic acid in the mixture of formic acid and water from step a) with a hydroxide in aqueous solution to produce a solution of a formate, wherein the organic material is an alpha-hydroxyaldehyde, an alpha-hydroxycarboxylic acid, a carbohydrate, or a glycoside.

2. The method according to claim 1, wherein the solution produced in step b) is concentrated in a step c) by separation of water by reverse osmosis and/or partial or complete evaporation of the water.

3. The method according to claim 1, further comprising adding water and/or the water separated in step c) to the reaction mixture to compensate for the water separated in step a).

4. The method according to claim 1, further comprising adding organic material to the reaction mixture to compensate for the reacted organic material.

5. The method according to claim 1, wherein the contact with the organic material and/or the separation as vapor according to step a) occurs at a temperature of 15 to 119.5° C.

6. The method according to claim 1, wherein the separation as vapor according to step a) takes place at a pressure that is reduced with respect to atmospheric pressure.

7. The method according to claim 1, wherein the condensation of the vapor according to step a) occurs by introducing the vapor into water, an aqueous solution, or the aqueous solution according to step b).

8. The method according to claim 1, wherein the hydroxide is ammonium hydroxide, aluminum hydroxide, copper hydroxide, nickel hydroxide, an alkaline earth metal hydroxide, an alkali metal hydroxide, calcium hydroxide, magnesium hydroxide, sodium hydroxide, potassium hydroxide, or cesium hydroxide.

9. The method according to claim 1, wherein the hydroxide in step b) is used in such a stoichiometric ratio to the formic acid that it is reacted completely.

10. The method according to claim 1, wherein $n=3+Y$.

11. The method according to claim 1, wherein the contact with the organic material and/or separation as vapor according to step a) occurs at a temperature of 40 to 95° C.

12. The method according to claim 1, wherein the contact with the organic material and/or separation as vapor according to step a) occurs at a temperature of 50 to 85° C.

13. The method according to claim 1, wherein the contact with the organic material and/or separation as vapor according to step a) occurs at a temperature of 55 to 85° C.

14. The method according to claim 1, wherein the contact with the organic material and/or separation as vapor according to step a) occurs at a temperature of 60 to 83° C.

15. The method of claim 1, wherein in step a) the organic material and the catalyst remain in the reaction mixture.

16. The method of claim 1, wherein step a) and step b) do not interrupt the formation of formic acid in the reaction mixture.

* * * * *